United States Patent [19]
Yasuda et al.

[11] Patent Number: 5,973,142
[45] Date of Patent: Oct. 26, 1999

[54] PROCESS FOR SYNTHESIZING CARBAPENEM INTERMEDIATES

[76] Inventors: Nobuyoshi Yasuda; Chunhua Yang, both of c/o Merck & Co., Inc. P.O. Box 2000, 126 E. Lincoln Ave., Rahway, N.J. 07065

[21] Appl. No.: 09/005,158

[22] Filed: Jan. 9, 1998

Related U.S. Application Data

[60] Provisional application No. 60/036,357, Jan. 21, 1997.
[51] Int. Cl.$^6$ ............... C07D 205/08; C07F 7/10; C09B 49/00
[52] U.S. Cl. ............................................. 540/200
[58] Field of Search ............................... 540/200

[56] References Cited

U.S. PATENT DOCUMENTS

| | | | |
|---|---|---|---|
| 4,377,591 | 3/1983 | Hiraoka | 540/200 |
| 4,960,879 | 10/1990 | Uyeo | 540/200 |
| 5,463,047 | 10/1995 | Schneider et al. | 540/362 |

FOREIGN PATENT DOCUMENTS 0 451 764 A1   10/1991   European Pat. Off. .

*Primary Examiner*—Mark L. Berch
*Attorney, Agent, or Firm*—James M. Hunter, Jr.; Sylvia A. Ayler; Mark R. Daniel

[57] ABSTRACT

A process of synthesizing a compound of formula 1:

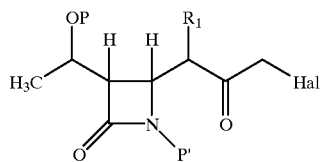

1 wherein P and P' each independently represent H or a protecting group, $R^1$ represents H or $C_{1-4}$ alkyl, and Hal represents a halogen selected from Cl, Br and I, comprising: reacting a compound of formula 2:

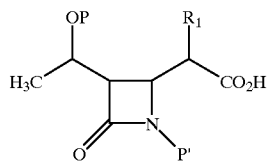

2 wherein P, P' and $R_1$ are as defined above with an N,O-di-$C_{1-4}$ alkyl hydroxylamine in the presence of a carbodiimide to produce a compound of formula 3:

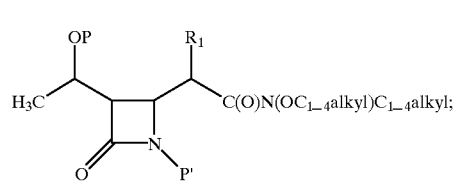

3 reacting compound 3 with a compound of formula 4:

$$MetCH_2SiR_2R_3R_4 \quad\quad 4$$

wherein Met represents lithium or halomagnesium;
$R_2$, $R_3$ and $R_4$ are $C_{1-4}$ alkyl or $C_{1-4}$ alkoxy, and the halo portion of halomagnesium is Cl, Br or I, to produce a compound of formula 5:

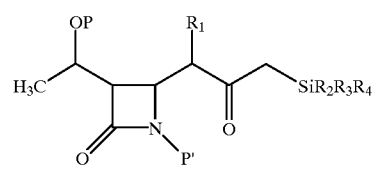

5 and
reacting compound 5 with a halogenating agent to produce a compound of formula 1.

17 Claims, No Drawings

PROCESS FOR SYNTHESIZING CARBAPENEM INTERMEDIATES

This application claims the benefit of U.S. Provisional Application No. 60/036,357, filed Jan. 21, 1997.

BACKGROUND OF THE INVENTION

The present invention relates to the synthesis of carbapenem intermediates. The invention is particularly useful in that it facilitates the presence of a 1β-methyl group upon cyclization to form the non-beta lactam ring of the carbapenem nucleus.

The side chain which is attached at position two of the carbapenem nucleus can be introduced prior to non-beta lactam ring cyclization. This reduces the number of steps which are necessary to produce the final compound. The side chain can be in protected or unprotected form, or a precursor of the side chain can be used, such as a coupling moiety, which can be present in protected or unprotected form prior to cyclization. This facilitates the addition of the side chain. Thus, the process described herein has extended utility, in that many different carbapenem antibiotics can be synthesized.

These and other objects and advantages will be apparent from the teachings contained herein.

SUMMARY OF THE INVENTION

A process of synthesizing a compound of formula 1 is described:

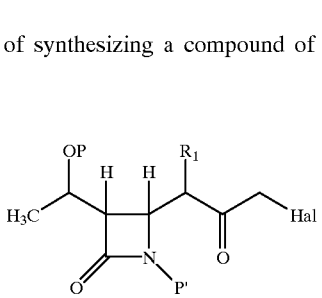

wherein P and P' independently represent H or a protecting group, $R^1$ represents H or $C_{1-4}$ alkyl, and Hal represents a halogen selected from Cl, Br and I, comprising:
reacting a compound of formula 2:

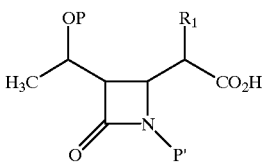

wherein P, P' and $R_1$ are as defined above with a di-$C_{1-4}$ alkyl hydroxylamine in the presence of a carbodiimide to produce a compound of formula 3:

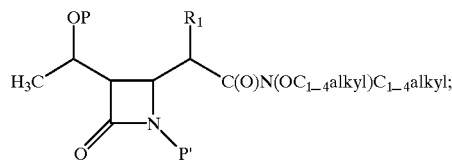

reacting compound 3 with a compound of formula 4:

wherein Met represents lithium or halomagnesium, and $R_2$, $R_3$ and $R_4$ are $C_{1-4}$ alkyl or $C_{1-4}$ alkoxy, and the halo portion of halomagnesium is Cl, Br or I,
to produce a compound of formula 5:

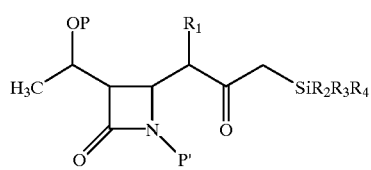

and reacting compound 5 with a halogenating agent to produce a compound of formula 1.

DETAILED DESCRIPTION OF THE INVENTION

The invention is described herein in detail using the terms defined below unless otherwise specified.

Hal and halo mean Cl, Br and I selected on an independent basis.

Preferred alkyl groups include methyl, ethyl, n-propyl, isopropyl, n-butyl and t-butyl. More preferred alkyl groups are methyl, ethyl, isopropyl and t-butyl.

The term "carbodiimide" is used in the conventional sense and refers to compounds which contain the moiety: —NH=C=NH—. Examples include 1-(3-dimethylaminopropyl)-3-ethylcarbodiimide (EDC) and 1,3-dicyclohexylcarbodiimide (DCC).

The intermediate compounds synthesized in the present invention have asymmetric centers and occur as racemates, racemic mixtures, and as individual diastereomers. The processes of synthesizing all such isomers, including optical isomers, are included in the present invention.

In the invention described herein, a process of synthesizing a compound of formula 1 is conducted.

P and P' each independently represent H or a protecting group. $R_1$ represents H or $C_{1-4}$ alkyl, and Hal represents a halogen selected from Cl, Br and I.

A compound of formula 2:

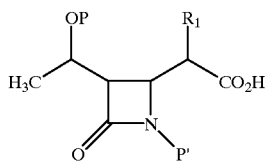

wherein P, P' and R₁ are as defined above is reacted with a di($C_{1-4}$) alkyl hydroxylamine in the presence of a carbodiimide to produce a compound of formula 3:

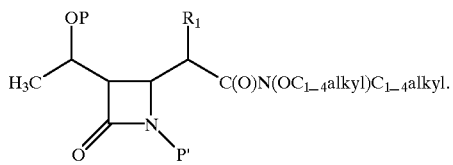

Compound 3 is reacted with a silyl compound of formula 4:

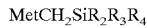    4 in which Met represents lithium or halomagnesium. The halo portion of halomagnesium is Cl, Br or I. $R_2$, $R_3$ and $R_4$ are independently $C_{1-4}$ alkyl or $C_{1-4}$ alkoxy. This produces a compound of formula 5:

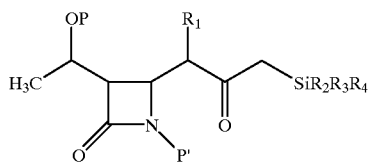

Compound 5 is reacted with a halogenating agent to produce a compound of formula 1.

Certain intermediate compounds are also included in the present invention. In one aspect of the invention, a compound represented by the formula 1":

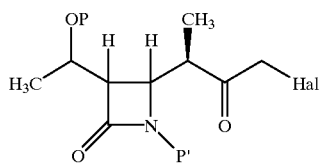

is included wherein P and P' each independently represent H or a protecting group and Hal represents a halogen selected from Cl, Br and I.

In another aspect of the invention, a compound represented by formula 3 or 5:

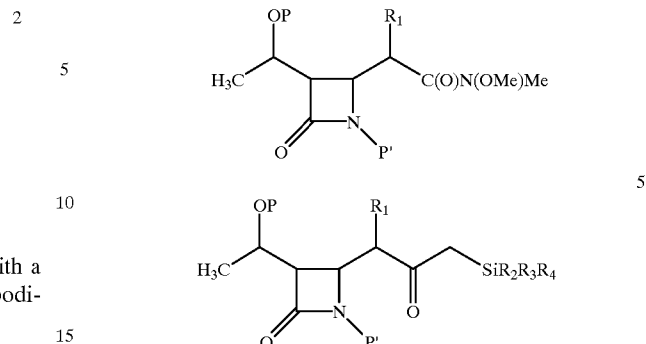

is included wherein:

$R_1$ represents H or $C_{1-4}$ alkyl,

P and P' independently represent H or a protecting group, and $R_2$, $R_3$ and $R_4$ are $C_{1-4}$ alkyl or $C_{1-4}$ alkoxy.

In a preferred aspect of the invention, P' represents H.

In another preferred aspect of the invention, $R_1$ represents $C_{1-4}$ alkyl, preferably, $R_1$ represents methyl, and most preferably methyl in the beta configuration.

In another preferred aspect of the invention, the carbodiimide is selected from EDC and DCC. Most preferably, the carbodiimide is EDC.

In another preferred aspect of the invention, zero or one of $R_2$, $R_3$ and $R_4$ represents $C_{1-4}$ alkoxy, and the others represent $C_{1-4}$ alkyl. More preferably, $R_2$, $R_3$ and $R_4$ represent methyl, or one of these variables represents methoxy or isopropyloxy, and the others represent methyl.

In another preferred aspect of the invention, the halo portion of halomagnesium is Cl.

In another preferred aspect of the invention, the halogenating agent is selected from the group consisting of $Br_2$, $I_2$, $Cl_2$, ICl, $SO_2Cl_2$, N-chlorosuccinimide (NCS) and N-bromosuccinimide (NBS).

In a more preferred aspect of the invention, the halogenating agent is $Br_2$, ICl or $SO_2Cl_2$.

A preferred process of synthesizing a compound of formula 1:

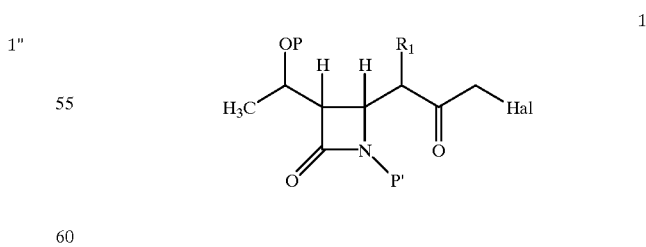

is included wherein P and P' each independently represent H or a protecting group, $R^1$ represents H or $C_{1-4}$ alkyl, and Hal represents a halogen selected from Cl, Br and I, which comprises: reacting a compound of formula 2:

A compound of formula 2:

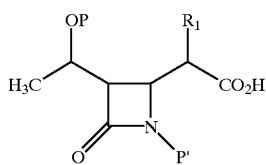
2 wherein P, P' and $R_1$ are as defined above with N,O-dimethylhydroxylamine in the presence of EDC or DCC to produce a compound of formula 3:

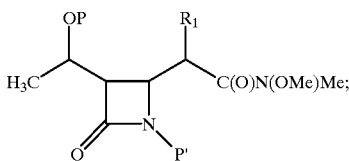
3 reacting compound 3 with a compound of formula 4:

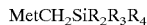
MetCH$_2$SiR$_2$R$_3$R$_4$    4 wherein Met represents lithium or halomagnesium, and $R_2$, $R_3$ and $R_4$ are $C_{1-4}$ alkyl or $C_{1-4}$ alkoxy, and the halo portion of halomagnesium is Cl, Br or I, to produce a compound of formula 5:

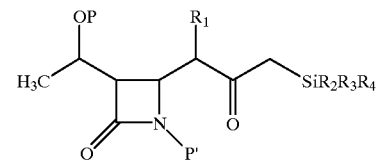
5 and reacting compound 5 with a halogen selected from Br$_2$, I$_2$, Cl$_2$, NCS, NBS, ICl and SO$_2$Cl$_2$ to produce a compound of formula 1.

A more preferred process is set forth below.

A compound of formula 1':

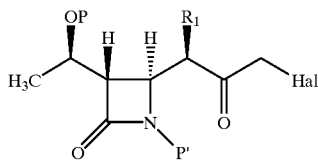
1' wherein P and P' each independently represent H or a protecting group, $R^1$ represents H or $C_{1-4}$ alkyl, and Hal represents a halogen selected from Cl, Br and I.

A compound of formula 2':

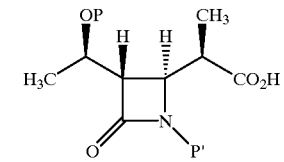
2' wherein P, P' and $R_1$ are as defined above is reacted with N,O-dimethylhydroxylamine in the presence of 1-(3-dimethylaminopropyl)- 3-ethylcarbodiimide (EDC) or 1,3-dicyclohexylcarbodiimide (DCC) to produce a compound of formula 3':

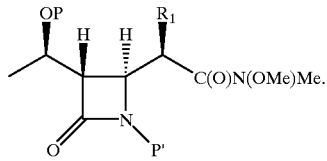
3'

Compound 3' is reacted with a silyl compound of formula 4:

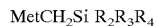
MetCH$_2$Si R$_2$R$_3$R$_4$    4

Met represents lithium or halomagnesium, the halo portion of halomagnesium is Cl, Br or I, and $R_2$, $R_3$ and $R_4$ are independently $C_{1-4}$ alkyl or $C_{1-4}$ alkoxy. This produces a compound of formula 5':

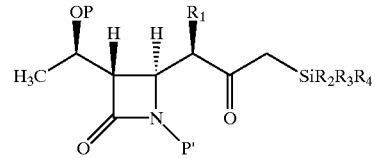
5'

Compound 5' is reacted with a halogenating agent selected from Br$_2$, I$_2$, Cl$_2$, NBS, NCS, ICl and SO$_2$Cl$_2$ to produce a compound of formula 1'.

The hydroxyl group at the 8-position of the carbapenem and the nitrogen in the beta lactam ring may be blocked until later in the synthesis, such as upon cyclization or when the final product is prepared. These blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with fluoride ion, treatment with a transition metal catalyst and a nucleophile, and catalytic hydrogenation.

Examples of suitable protecting groups are: t-butylmethylphenylsilyl, t-butyldiphenylsilyl, trimethylsilyl (TMS), triethylsilyl (TES), t-butyldimethylsilyl (TBDMS), o-nitrobenzyloxycarbonyl, p-nitrobenzyloxycarbonyl (PNZ), p-nitrobenzyl (PNB), benzyloxycarbonyl, t-butyloxycarbonyl, 2,2,2-trichloroethyloxycarbonyl and allyloxycarbonyl. Preferred hydroxyl protecting groups are TBDMS, TMS and TES.

Many other suitable protecting groups are known in the art. See, e.g., T. W. Greene, *Protective Groups in Organic Synthesis*, John Wiley & Sons, Inc., 1981 (Chapters 2 and 5).

Compound 1 is useful in the synthesis of carbapenem antibiotics. For example, compound 1 is useful in the synthesis of carbapenems such as those disclosed in EP Publication No. 0 451 764 A1 published on Oct. 16, 1991 and incoroporated herein by reference, as well as other carbapenems.

The invention is illustrated in connection with the following non-limiting examples.

EXAMPLE 1

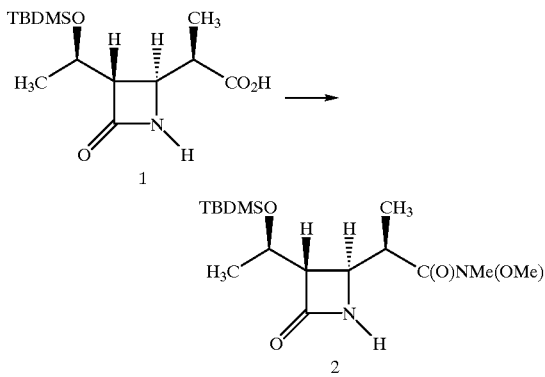

To a mixture of 1 (25.0 g), N,O-dimethylhydroxyamine hydrochloride (12.1 g), 1-hydroxybenzotriazole monohydrate (HOBT) (16.8 g), and 1-(3-dimethylaminopropyl)-3-ethylcarbodiimide hydrochloride (EDC) (23.8 g) in a mixture of water (150 mL) and methylene chloride (100 mL) was slowly added a solution of triethylamine (17.5 mL) in methylene chloride (50 mL) at ambient temperature. After stirring at ambient temperature overnight, additional N,O-dimethylhydroxyamine hydrochloride (1.6 g), 1-hydroxybenzotriazole monohydrate (2.7 g), triethylamine (2.4 mL), and 1-(3-dimethylaminopropyl)-3-ethylcarbodiimide hydrochloride (3.2 g) were added to the reaction mixture at ambient temperature. After confirming completion of the reaction by HPLC, the reaction mixture was diluted with a mixture of methylene chloride (45 mL) and saturated aqueous sodium hydrogen carbonate (45 mL).

The organic layer was separated, subsequently washed with 0.5 M phosphate buffer (140 mL) twice and saturated aqueous sodium chloride (140 mL), dried over magnesium sulfate, concentrated in vacuo. The residue was crystallized from ethyl acetate and hexanes to give crystalline 2 (28.0 g).

$^1$H NMR (250 MHz; CDCl$_3$): δ 5.98 (broad s, 1 H), 4.17 (m, 1 H), 3.84 (dd, J=4.9 and 2.2 Hz, 1 H), 3.69 (s, 3 H), 3.18 (s, 3 H), 3.15 (m, 1 H), 2.98 –2.95 (m, 1 H), 1.19 (d, J=6.9 Hz, 3 H), 1.18 (d, J=6.2 Hz, 3 H), 0.86 (s, 9 H), and 0.06 (s, 6 H).

$^{13}$C NMR (62.9 MHz: CDCl$_3$): δ 175.2, 168.5, 65.2, 61.4, 61.3, 52.1, 37.7, 31.9, 25.7, 22.3, 17.8, 12.4, –4.4, and –5.1.

EXAMPLE 2

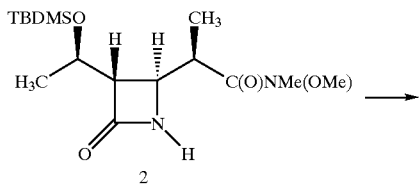

-continued

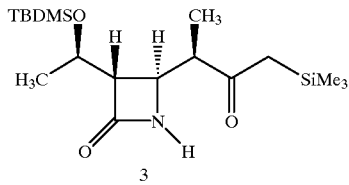

To a solution of 2 (3.4 g) in dry tetrahydrofuran (30 mL) was slowly added a solution of trimethylsilylmethyllithium (1 M hexanes; 35 mL) at –45° C. After the completion of the addition, the mixture was allowed to be warmed up to –10° C. The reaction was complete in 20 minutes at –10° C. The reaction mixture was cooled down to –40° C. and a solution of acetic acid (2 M) in dry tetrahydrofuran (17 mL) was added to the mixture at –40° C. The resulted mixture was diluted with dry tetrahydrofuran (8 mL) at –40° C. After stirred for 20 minutes at –40° C., the reaction mixture was diluted with a mixture of diethyl ether (15 mL) and 0.5 M phosphate buffer (pH=7.0; 15 mL). The organic layer was separated, washed with 0.5 M phosphate buffer (pH=7.0; 15 mL), dried over magnesium sulfate, and concentrated in vacuo to give crude 3 (3.8 g). This compound was used for the next step without further purification.

Purified compound 3 (1.3 g) can be obtained by trituration of amide 3 (1.9 g) in hexanes (5 mL) at 0° C.

$^1$H NMR (250 MHz; CDCl$_3$): δ 5.98 (broad s, 1 H); 4.16 (m, 1 H), 3.84 (m, 1 H), 2.85 (m, 1H), 2.71 (m, 1 H), 2.32 (d, J=10.6 Hz, 1 H), 2.22 (d, J=10.6 Hz, 1 H); 1.18 (d, J=6.2 Hz, 3 H), 1.13 (d, J=7.2 Hz, 3 H), 0.85 (s, 9 H), 0.118 (s, 3 H), 0.116 (s, 6 H), and 0.05 (s, 6 H).

$^{13}$C NMR (62.9 MHz; CDCl$_3$): δ 211.5, 168.2, 65.5, 61.3, 51.1, 48.9, 37.8, 25.7, 22.5, 17.9, 11.1, –0.9, –4.3, and –5.0.

EXAMPLE 3

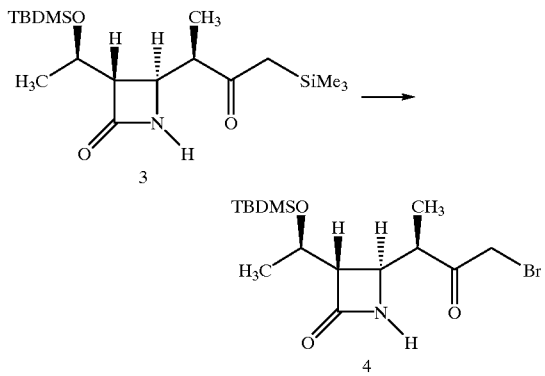

To a solution of 3 (3.76 g) in dry methylene chloride (35 mL) was slowly added a solution of bromine (2 M; 4.8 mL) in dry methylene chloride at –35° C. The reaction mixture was allowed to be warmed up to –5° C. The mixture was cooled down to –35° C. and additional the bromine solution (2 M; 1.2 mL) was added to the mixture. The mixture was stirred between –30 and –5° C. for 20 minutes. The reaction mixture was diluted with a mixture of methylene chloride (35 mL) and 0.5 M phosphate buffer (pH=7.0; 35 mL). The organic layer was separated, subsequently washed with water (35 mL), 0.1 M sodium thiosulfate (35 mL) and water (35 mL), dried over magnesium sulfate, and concentrated in vacuo to give crude 4 (3.81 g). This compound could be used for the preparation of the biologically active carbapenems, without further purification. Analytically pure compound was obtained by silica gel column chromatography.

¹H NMR (250 MHz; CDCl₃): δ 5.87 (broad s, 1 H), 4.17 (m, 1 H), 3.99 (d, J=12.5 Hz, 1 H), 3.92 (d, J=12.5 Hz, 1 H), 3.90 (dd, J=4.9 and 2.2 Hz, 1 H), 3.24 (m, 1 H), 2.94 (dd, J=5.0 and 2.3 Hz, 1 H), 1.23 (d, J=7.2 Hz, 3 H), 1.19 (d, J=6.4 Hz, 3 H), 0.87 (s, 9 H), 0.07 (s, 3 H), and 0.06 (s, 3 H).

¹³C NMR (62.9 MHz; CDCl₃): δ 203.8, 168.3, 65.3, 61.8, 51.4, 45.4, 33.5, 25.7, 22.5, 17.9, 12.5, −4.3, and −5.0.

EXAMPLE 4

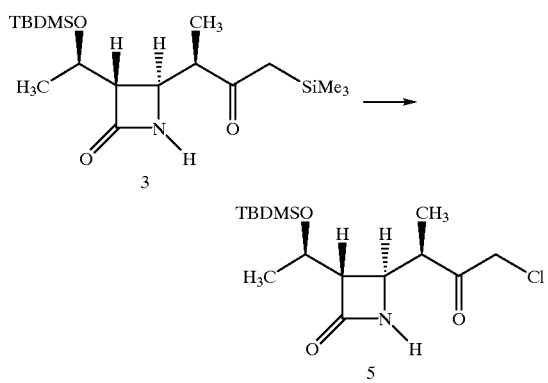

To a solution of 3 (1.88 g) in dry methylene chloride (15 mL) was slowly added a solution of sulfuryl chloride (2 M; 3.1 mL) in dry methylene chloride at −30° C. The mixture was stirred between −30 and −10° C. for 20 minutes. The reaction mixture was diluted with methylene chloride (15 mL) and 0.5 M phosphate buffer (15 mL). The organic layer was separated, subsequently washed with water (15 mL), 0.1 M sodium thiosulfate (15 mL) and water (15 mL), dried over magnesium sulfate, and concentrated in vacuo to give crude 5 (2 g). This compound was purified by trituration with cold hexanes (5 mL) to give pure 5 (1.3 g).

¹H NMR (250 MHz; CDCl₃): δ 5.89 (broad s, 1 H), 4.17 (m, 1 H), 4.15 (s, 2 H), 3.89 (dd, J=4.7 and 2.3 Hz, 1 H), 3.20 (m, 1 H), 2.92 (dd, J=4.9 and 2.3 Hz, 1 H), 1.22 (d, J=7.3 Hz, 3 H), 1.19 (d, J=6.7 Hz, 3 H), 0.87 (s, 9 H), 0.07 (s, 3 H), and 0.06 (s, 3 H).

¹³C NMR (62.9 MHz; CDCl₃): δ 204.4, 168.3, 65.3, 61.7, 51.3, 47.6, 45.0, 25.7, 22.5, 17.9, 12.2, −4.3, and −5.0.

EXAMPLE 5

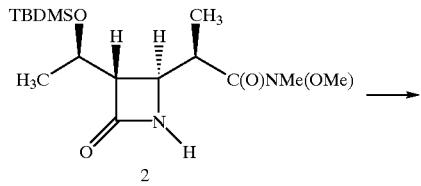

To a solution of 2 (52 mg) in dry tetrahydrofuran (2 mL) was added a solution of (isopropyloxydimethylsilyl)methylmagnesium chloride (0.7 M; 1.1 mL) in diethyl ether under ice-cooling. After the mixture was stirred under the ice bath for 2 hours, additional (isopropyloxydimethylsilyl)methylmagnesium chloride (0.7 M; 0.5 mL) in diethyl ether was added. After additional 1 hour under the ice bath, to the mixture was added saturated aqueous ammonium chloride (5 mL). The mixture was extracted with ethyl acetate (20 mL), dried over magnesium sulfate, purified by a silica gel column chromatography to give 6 (41 mg).

¹H NMR (250 MHz; CDCl₃): δ 6.02 (broad s, 1 H), 4.17 (m, 1 H), 4.01 (q, J=6.0 Hz, 1 H), 3.86 (dd, J=4.4 and 2.2 Hz, 1 H), 2.88 (dd, J=4.2 and 2.2 Hz, 1 H), 2.83 (m, 1 H), 2.38 (d, J=10.8 Hz, 1 H), 2.25 (d, J=10.8 Hz, 1 H), 1.17 (d, J=6.4 Hz, 3 H), 1.134 (d, J=6.0 Hz, 6 H), 1.125 (d, J=7.1 Hz, 3 H), 0.85 (s, 9 H), 0.20 (s, 6 H), and 0.04 (s, 6 H).

¹³C NMR (62.9 MHz; CDCl₃): δ 211.0, 168.4, 65.7, 65.2, 61.3, 50.9, 49.0, 38.5, 25.7, 25.6, 22.5, 17.9, 11.4, −0.66, −0.70, −4.3, and −5.0.

While certain preferred embodiments have been described herein in detail, numerous alternative embodiments are contemplated as falling within the scope of the appended claims.

What is claimed is:

1. A process of synthesizing a compound of formula 1:

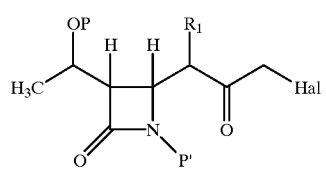

wherein P and P' each independently represent H or a protecting group, R¹ represents H or C₁₋₄ alkyl, and Hal represents a halogen selected from Cl, Br and I, comprising:

reacting a compound of formula 2:

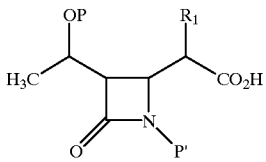

wherein P, P' and $R_1$ are as defined above with a N,O di-$C_{1-4}$ alkyl hydroxylamine in the presence of a carbodiimide to produce a compound of formula 3:

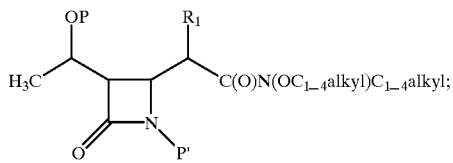

reacting compound 3 with a compound of formula 4:

    4 wherein Met represents lithium or halomagnesium;
  $R_2$, $R_3$ and $R_4$ are $C_{1-4}$ alkyl or $C_{1-4}$ alkoxy, and the halo portion of halomagnesium is Cl, Br or I,
to produce a compound of formula 5:

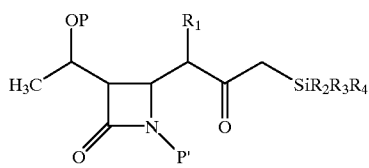

and
  reacting compound 5 with a halogenating agent to produce a compound of formula 1.
2. A process of synthesizing a compound of formula 1:

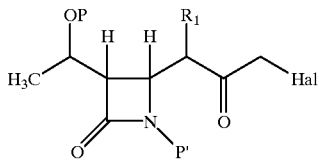

in accordance with claim 1 wherein $R_2$ and $R_3$ are selected from methyl, ethyl, n-propyl, isopropyl, n-butyl and t-butyl, and $R_4$ represents $C_{1-4}$ alkoxy.

3. A process in accordance with claim 1 wherein $R_4$ represents isopropoxy.

4. A process in accordance with claim 1 wherein P and P' represent H.

5. A process in accordance with claim 1 wherein P represents a protecting group and P' represents H.

6. A process in accordance with claim 5 wherein P is selected from the group consisting of: t-butylmethylphenylsilyl, t-butyldiphenylsilyl, trimethylsilyl, triethylsilyl, t-butyldimethylsilyl, o-nitrobenzyloxycarbonyl, p-nitrobenzyloxycarbonyl, p-nitrobenzyl, benzyloxycarbonyl, t-butyloxycarbonyl, 2,2,2-trichloroethyloxycarbonyl and allyloxycarbonyl.

7. A process in accordance with claim 6 wherein P represents a member selected from t-butyldimethylsilyl, trimethylsilyl and triethylsilyl.

8. A process in accordance with claim 1 wherein $R^1$ represents $C_{1-4}$ alkyl.

9. A process in accordance with claim 8 wherein $R^1$ represents methyl.

10. A process in accordance with claim 1 wherein the di-$C_{1-4}$ alkyl hydroxylamine is N,O-dimethylhydroxyamine.

11. A process in accordance with claim 1 wherein the carbodiimide is selected from 1-(3-dimethylaminopropyl)-3-ethylcarbodiimide and 1,3-dicyclohexylcarbodiimide.

12. A process in accordance with claim 1 wherein compound 5 is reacted with a halogenating agent selected from $Br_2$, $I_2$, $Cl_2$, N-chlorosuccinimide, N-bromosuccinimide, ICl and $SO_2Cl_2$ to produce a compound of formula 1.

13. A process in accordance with claim 12 wherein the halogenating compound is $Br_2$.

14. A process in accordance with claim 12 wherein the halogenating agent is $SO_2Cl_2$.

15. A process of synthesizing a compound of formula 1:

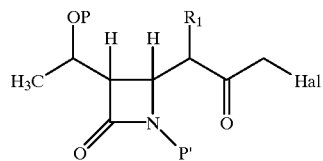

wherein P and P' independently represent H or a protecting group, $R^1$ represents H or $C_{1-4}$ alkyl, and
  Hal represents a halogen selected from Cl, Br and I, which comprises:
    reacting a compound of formula 2:

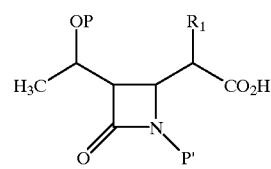

wherein P, P' and $R_1$ are as defined above with N,O-dimethylhydroxylamine in the presence of EDC (1-(3-dimethylaminopropyl)-3-ethylcarbodiimide hydrochloride) or DCC (1,3-dicyclohexylcarbodiimide) to produce a compound of formula 3:

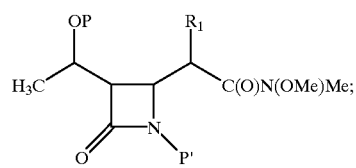

reacting compound 3 with a compound of formula 4:

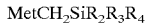    4 wherein Met represents lithium or halomagnesium, and $R_2$, $R_3$ and $R_4$ are $C_{1-4}$ alkyl or $C_{1-4}$ alkoxy, and the halo portion of halomagnesium is Cl, Br or I, to produce a compound of formula 5:

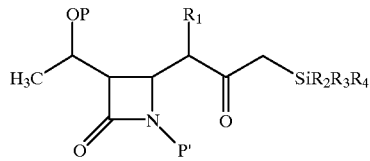

and reacting compound 5 with a halogenating agent selected from $Br_2$, $Cl_2$, $ICl$, $SO_2Cl_2$, NCS and NBS to produce a compound of formula 1.

16. A process of synthesizing a compound of formula 1':

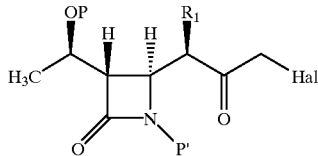

wherein P and P' each independently represent H or a protecting group, $R^1$ represents H or $C_{1-4}$ alkyl, and Hal represents a halogen selected from Cl, Br and I, comprising:

reacting a compound of formula 2':

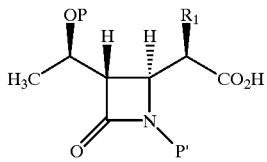

wherein P, P' and $R_1$ are as defined above with N,O-dimethylhydroxylamine in the presence of 1-(3-dimethylaminopropyl)-3-ethylcarbodiimide or 1,3-dicyclohexylcarbodiimide to produce a compound of formula 3':

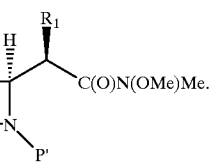

reacting a compound of formula 3' with a silyl compound of formula 4:

$$MetCH_2SiR_2R_3R_4 \quad 4$$

wherein Met represents lithium or halomagnesium,
the halo portion of halomagnesium is Cl, Br or I, and $R_2$, $R_3$ and $R_4$ are independently $C_{1-4}$ alkyl or $C_{1-4}$ alkoxy, to produce a compound of formula 5':

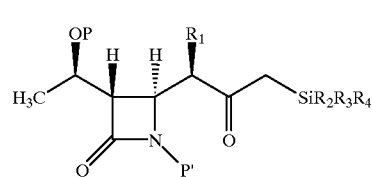

and reacting compound 5' with a halogenating agent selected from $Br_2$, $I_2$, $Cl_2$, NBS, NCS, ICl and $SO_2Cl_2$ to produce a compound of formula 1'.

17. A compound represented by formula 3 or 5:

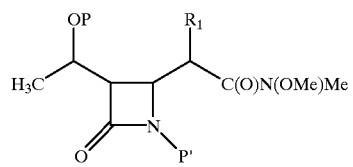

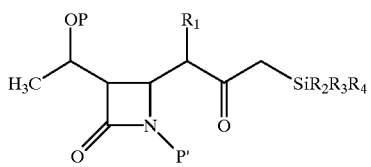

wherein
$R_1$ represents H or $C_{1-4}$ alkyl,
P and P' independently represent H or a protecting group, and $R_2$, $R_3$ and $R_4$ are $C_{1-4}$ alkyl or $C_{1-4}$ alkoxy.

* * * * *